US008193683B2

(12) United States Patent
Oguzman et al.

(10) Patent No.: US 8,193,683 B2
(45) Date of Patent: Jun. 5, 2012

(54) LOW POWER CONTINUOUS WAVE ULTRASOUND TRANSMITTER

(75) Inventors: Ismail H. Oguzman, Plano, TX (US); Myron J. Koen, Tucson, AZ (US)

(73) Assignee: Texas Instuments Incorporated, Dallas, TX (US)

(*) Notice: Subject to any disclaimer, the term of this patent is extended or adjusted under 35 U.S.C. 154(b) by 648 days.

(21) Appl. No.: 12/261,185

(22) Filed: Oct. 30, 2008

(65) Prior Publication Data
US 2010/0113934 A1    May 6, 2010

(51) Int. Cl.
*H01L 41/09*    (2006.01)
(52) U.S. Cl. .......................................... 310/317
(58) Field of Classification Search .................. 310/317
See application file for complete search history.

(56) References Cited

U.S. PATENT DOCUMENTS

| | | | |
|---|---|---|---|
| 6,135,961 A | 10/2000 | Pflugrath et al. | |
| 6,648,826 B2 | 11/2003 | Little et al. | |
| 7,604,596 B2 | 10/2009 | Hwang et al. | |
| 7,972,268 B2* | 7/2011 | Freiburger | 600/437 |
| 2002/0133076 A1* | 9/2002 | Amemiya | 600/453 |
| 2003/0163047 A1 | 8/2003 | Little et al. | |
| 2004/0113669 A1* | 6/2004 | Wodnicki | 327/170 |
| 2004/0133110 A1 | 7/2004 | Little et al. | |
| 2005/0265267 A1 | 12/2005 | Hwang | |
| 2007/0014190 A1* | 1/2007 | Fehl et al. | 367/138 |
| 2008/0027323 A1* | 1/2008 | Freiburger | 600/453 |
| 2008/0066552 A1* | 3/2008 | Amemiya | 73/602 |
| 2008/0238532 A1* | 10/2008 | Hanazawa et al. | 327/534 |
| 2010/0012119 A1 | 1/2010 | Sallak et al. | |
| 2010/0113925 A1* | 5/2010 | Koen et al. | 600/437 |
| 2010/0137720 A1* | 6/2010 | Hanazawa et al. | 600/459 |
| 2011/0063011 A1* | 3/2011 | Barlow | 327/328 |
| 2011/0088475 A1* | 4/2011 | Oguzman et al. | 73/632 |

OTHER PUBLICATIONS

B. Haider, "Power Drive Circuits for Medical Diagnostic Medical Ultrasound," IEEE Proceedings of the 18th international Symposium on Power Semiconductor Devices and ICs, Jun. 2006.
M. A. Averkiou, D. N. Roundhill and J. E. Powers, "A New Imaging Technique Based on the Nonlinear Properties of Tissues," IEEE Ultrasonics Symposium, 1997.
B. Haider and R. Y. Chiao, "Higher Order Nonlinear Ultrasonic Imaging," IEEE Ultrasonics Symposium, 1999.

* cited by examiner

*Primary Examiner* — Thomas Dougherty
(74) *Attorney, Agent, or Firm* — Steven A. Shaw; W. James Brady; Frederick J. Telecky, Jr.

(57) ABSTRACT

A system and method for providing a continuous wave ("CW") ultrasonic drive signal and a B-mode ultrasonic drive signal from an ultrasonic transmitter are disclosed herein. An ultrasonic transmitter includes a first shunt transistor and a second shunt transistor. The first shunt transistor shunts positive transmitter output voltage to ground. The second shunt transistor shunts negative transmitter output voltage to ground. The shunt transistors include control inputs that, when modulated, cause the shunt transistors to produce a CW ultrasonic drive signal on a transmitter output. The ultrasonic transmitter also includes a first CW control transistor coupled to the first shunt transistor, and a second CW control transistor coupled to the second shunt transistor. The first and second CW control transistors respectively provide negative and positive CW drive voltage to the first and second shunt transistors.

17 Claims, 3 Drawing Sheets

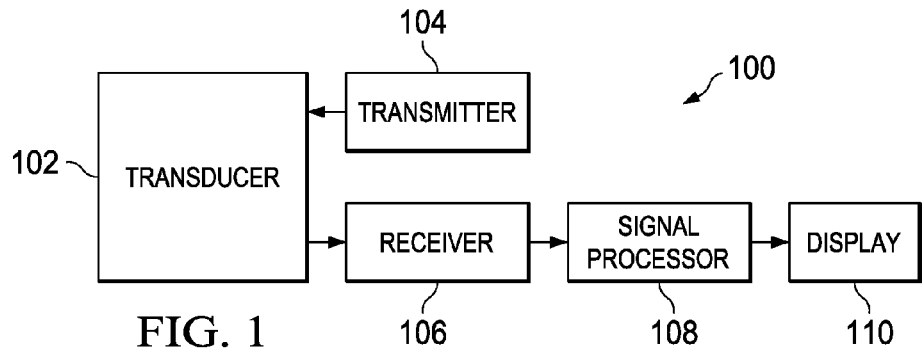
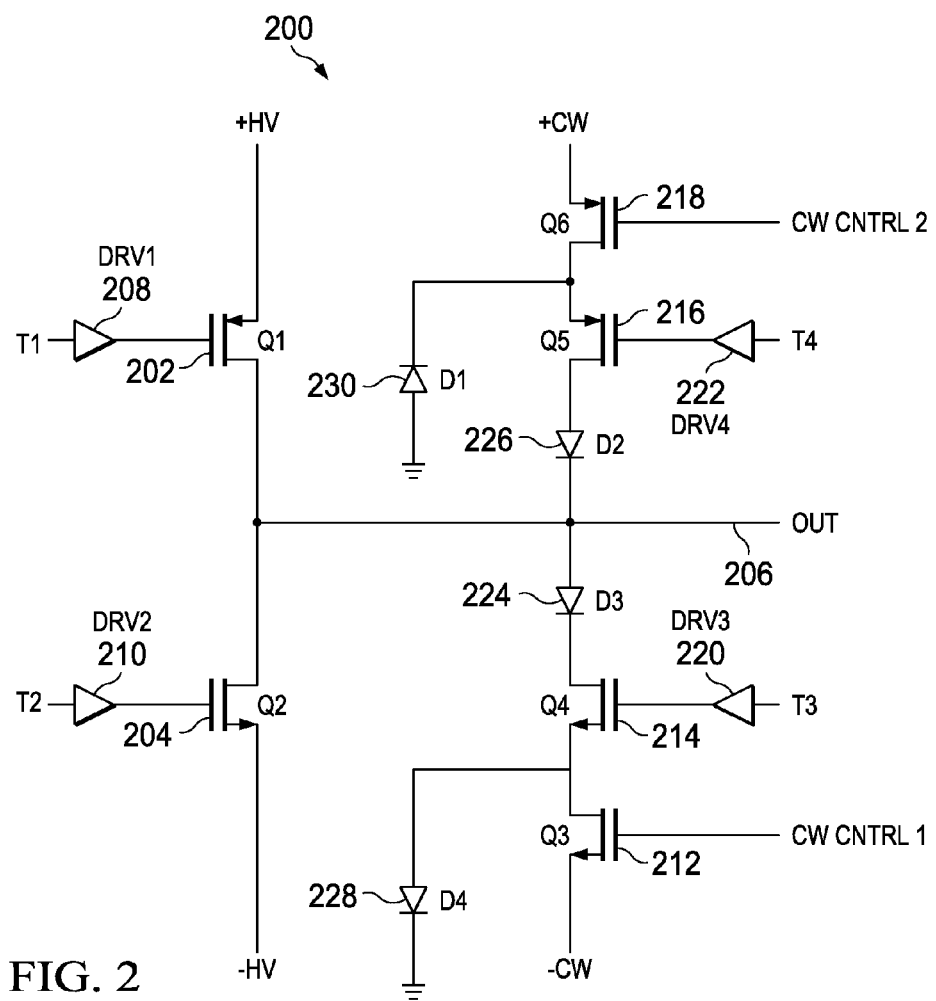

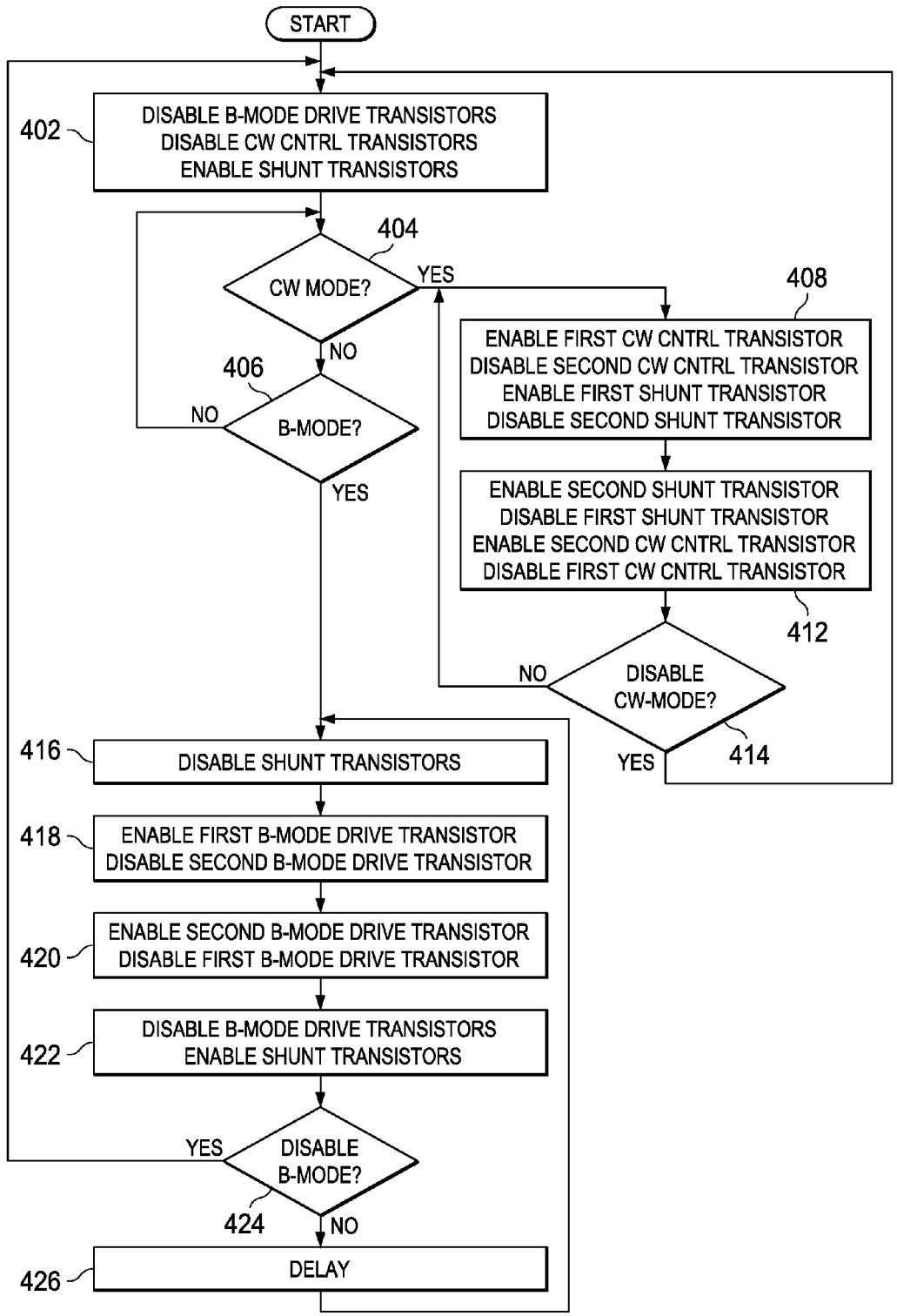

LOW POWER CONTINUOUS WAVE ULTRASOUND TRANSMITTER

CROSS REFERENCE TO RELATED APPLICATIONS

This application contains subject matter that may be related to U.S. patent application Ser. No. 12/261,209, U.S. Pat. No. 7,705,517 issued Apr. 27, 2010, entitled "Ultrasound Transmitter", U.S. patent application Ser. No. 12/261,252, entitled "Ultrasound Transmitter", and U.S. patent application Ser. No. 12/261,267, entitled "Ultrasound Transmitter".

BACKGROUND

Ultrasonic imaging has become a widely used tool in medical applications. Ultrasound techniques introduce high-frequency acoustic waves into a subject's body. The received echoes of those waves provide information allowing a trained observer to view the subject's internal organs.

Ultrasound medical diagnostic equipment can operate in a variety of modes. Continuous wave ("CW") is one such operational mode. In the CW operating mode, ultrasound energy is continuously generated and applied to a subject. An intra-body flow (e.g., flow within a blood vessel) introduces a Doppler shift in the reflected ultrasound energy. By detecting the Doppler shift in the received signal frequency, the velocity of the flow can be determined and the subject's cardiac health ascertained.

Another popular ultrasound operating mode is commonly referred to as "B-mode." The term "B-mode" derives from the assignment of display brightness value to each ultrasonic signal reflection in accordance with the amplitude of the reflection. B-mode employs a high-amplitude, short duration pulsed ultrasound signal to produce a two-dimensional image of the subject's internal organs. The B-mode signal enters the body of the subject, is reflected off the various internal organs, and finally, is detected by a receiver. The received signal is collected and processed to form the image.

Users of ultrasound imaging systems demand both power efficiency and reduced device size in modern ultrasound equipment. Thus, it is desirable to accommodate both B-mode and CW-mode operation in an ultrasound imager that reduces component count and power dissipation.

SUMMARY

Various systems and methods for implementing both B-mode and continuous wave ("CW") mode ultrasonic drivers in an ultrasound transmitter while reducing power consumption and circuit area are disclosed herein. In accordance with at least some embodiments, an ultrasound transmitter includes a first shunt transistor and a second shunt transistor. The first shunt transistor shunts positive transmitter output voltage to ground. The second shunt transistor shunts negative transmitter output voltage to ground. The shunt transistors include control inputs that, when modulated, cause the shunt transistors to produce a CW ultrasonic drive signal on a transmitter output.

In accordance with at least some other embodiments, a method includes enabling a CW control transistor, enabling a first CW drive transistor; disabling a second CW drive transistor; and providing a CW drive signal to an acoustic transducer to generate a pressure wave.

In accordance with yet other embodiments, an ultrasound imaging system includes an ultrasonic signal receiver and an ultrasonic signal transmitter. The ultrasonic signal transmitter includes means for generating a CW ultrasonic drive signal from a transmitter shunt transistor.

BRIEF DESCRIPTION OF THE DRAWINGS

For a detailed description of exemplary embodiments of the invention, reference will now be made to the accompanying drawings in which:

FIG. 1 shows a block diagram of an exemplary ultrasound imaging system in accordance with various embodiments;

FIG. 2 shows an exemplary ultrasound transmitter that provides B-mode and CW-mode drive signals in accordance with various embodiments;

FIG. 4 shows a flow diagram for a method for generating CW-mode and B-mode ultrasonic drive signals in accordance with various embodiments.

NOTATION AND NOMENCLATURE

Figure 3:
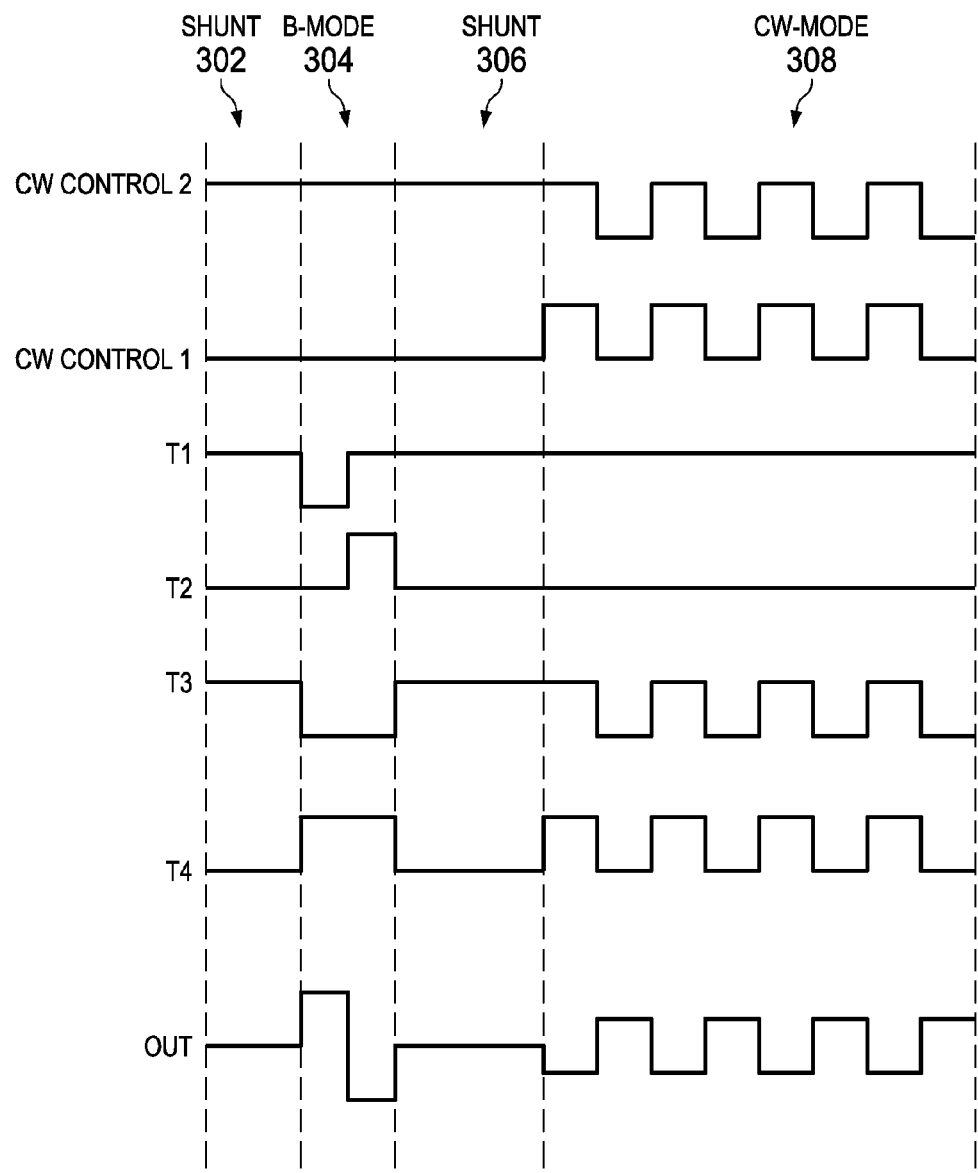
FIG. 3 shows a diagram of various signals produced when generating B-mode and CW-mode ultrasonic drive signals in accordance with various embodiments.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . . " Also, the term "couple" or "couples" is intended to mean either an indirect or direct electrical connection. Thus, if a first device couples to a second device, that connection may be through a direct electrical connection, or through an indirect electrical connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As ultrasonic imaging devices become smaller and more portable, it is desirable to reduce the power and component area consumed by the various circuits within those devices. Embodiments of the present disclosure employ ultrasonic signal transmitters featuring reduced circuit size and power consumption while providing both continuous wave ("CW") and B-mode ultrasonic drive signals. These advantages are achieved, at least in part by adapting the transmitter shunt transistors to operate as CW-mode drivers.

FIG. 1 shows a block diagram of an exemplary ultrasound imaging system 100 in accordance with various embodiments. The terms "ultrasound" or "ultrasonic" generally refer to acoustic waves at frequencies beyond the range of human hearing (e.g., frequencies above 20 KHz). The system 100 comprises a transducer 102, a transmitter 104, a receiver 106, a signal processor 108, and a display 110. The transducer 102 converts the electrical drive signals generated by the transmitter 104 into sound waves (i.e., pressure waves) that are introduced into the subject to be imaged, for example, a human body when considering medical ultrasound. The transducer 102 can comprise a piezoelectric crystal, electromagnetic transducer, micro-electro-mechanical system ("MEMS") transducer or other device that converts an electrical signal into sound waves. Moreover, the transducer 102 can comprise one or more transducer elements. The transducer 102 also detects ultrasonic waves reflected by internal structures of the subject and converts the detected waves into electrical signals. In some embodiments, the same transducer elements are used to generate ultrasonic waves and to detect ultrasonic waves. In other embodiments, separate transducer elements are used for wave generation and detection.

The transmitter 104 is coupled to the transducer 102. The transmitter 104 produces an oscillating electrical signal at a frequency and amplitude suitable for imaging desired structures internal to the subject. For example, transmitter output signals for use in imaging the internal organs of a human body may range from 1 to 20 megahertz with lower frequencies providing lower resolution and greater imaging depth. The transmitter 104, while not limited to any particular signal amplitudes, may provide, for example, a drive signal amplitude in the range of +/−75 volts for B-mode sonography and a drive signal in the range of +/−5 volts for CW sonography. The transmitter 104 employed in embodiments of the present disclosure advantageously uses transmitter circuitry that merges the CW drive and output shunt components, as described herein, to reduce the size and power consumption of the transmitter 104.

The receiver 106 is coupled to the transducer 102. As explained above, the transducer 102 detects ultrasonic waves reflected by subject internal structures. The transducer 102 converts the detected waves into electrical signals. The electrical signals are provided to the receiver 106. The receiver 106 performs initial processing of the received signals. Processing performed by the receiver 106 can comprise, for example, amplifying, filtering, digitizing, etc.

The signal processor 108 is coupled to the receiver 106. The signal processor 108 may, for example, provide further filtering of received signals, detect signal reflections, and prepare output signals for display on the display 110. The signal processor 108 may comprise, for example, a digital signal processor or other microprocessor or microcomputer and associated software programming along with attendant memory and interface devices, or dedicated hardware circuitry adapted to perform the processing functions. The display 110 may be a liquid crystal display, a cathode ray display, or any other suitable display device.

FIG. 2 shows exemplary ultrasound transmitter circuitry 200 that provides B-mode ultrasonic drive signals and CW-mode ultrasonic drive signals while reducing the size and power consumption of the transmitter 104 in accordance with various embodiments. The transmitter 200 includes a B-mode driver and a CW-mode driver. The B-mode driver comprises transistors Q1 202 and Q2 204 and associated transistor drivers 208, 210. The CW-mode driver comprises transistors Q3 212, Q4 214, Q5 216, Q6 218, transistor drivers 220, 222, and diodes D1 230, D2 226, D3 224, and D4 228. Both the B-mode driver and the CW-mode driver are coupled to the transmitter output 206.

When the transmitter circuit 200 is configured for B-mode operation, transistors Q1 202 and Q2 204 are used to a high voltage signal on output 206. Transistor Q1 202 is turned on and transistor Q2 204 is turned off, to allow development of voltage +HV (e.g., 75 volts) on the output 206. Note that the voltage developed on output 206 may be less than +HV due to various circuit voltage drops. Driver 208 holds transistor Q1 202 on for a predetermined duration to produce one-half cycle of a B-mode pulse. At the expiration of the half-cycle time duration, transistor Q1 202 is turned off, and transistor Q2 204 is turned on allowing development of −HV (e.g., −75 volts) on the output 206. As described above, the voltage developed on the output 238 is conditioned on circuit voltage drops. Driver 210 holds transistor Q2 204 on for a predetermined duration to produce one-half cycle of a B-mode pulse. Thus, some embodiments generate a desired number of B-mode cycles by alternately turning the transistors Q1 202 and Q2 204 on and off. Some embodiments activate transistors Q4 214 and Q5 216 following completion of each half-cycle (while both Q1 202 and Q2 204 are off) to clamp the output 206 to ground between half-cycles. Some embodiments generate pulses of one polarity by repetitively enabling and disabling only one of Q1 202 and Q2 204 with clamping (at least one of Q4 214 and Q5 216 turned on) during the disabled intervals. When a desired number of cycles have been generated, both transistors Q1 202 and Q2 204 are turned off, and a portion of the CW-mode driver, specifically transistors Q4 214 and Q5 216, can be activated to clamp the output 206 to ground. Transistors Q3 212 and Q6 218, the CW control transistors, preferably remain off during both B-mode operation, and clamping as described above.

Transistors Q1 202 and Q2 204 may preferably feature a low on resistance to effectively drive the transducer 102. For example, the load resistance seen by transistors Q1 202 and Q2 204 may be in the 100 ohm range, and the load may be shunted with as much as 300 pico-farads of capacitance. Accordingly, the on resistance of transistors Q1 202 and Q2 204 may preferably be in the range of 8 ohms. Transistors Q4 214 and Q5 216 preferably need not be as large (i.e., have as low an on resistance) as transistors Q1 202 and Q2 204 in order to discharge the capacitance of the output 206. Moreover, the input capacitance of transistors Q1 202 and Q2 204 may be higher than the input capacitance of transistors Q4 214 and Q5 216. Consequently, the drive current required of drivers 208, 210 may be higher than the drive current required of drivers 220, 222.

When the transmitter circuit 200 is configured for CW-mode operation, the B-mode drive transistors Q1 202 and Q2 204 are turned off. Activating the CW control transistor Q6 218 allows development of voltage +CW on the circuit node connecting Q6 218 and Q5 216. Activating the CW control transistor Q3 212 allows development of voltage −CW on the circuit node connecting Q3 212 and Q4 214. Voltages +/−CW are preferably lower than voltages +/−HV, for example, +/−CW may be +/−5 volts respectively. To produce a first half-cycle of a CW-mode drive signal on the output 206, CW drive transistor Q4 214 and CW CNTRL transistor Q3 212 are turned on while transistors Q5 216 and Q6 218 are turned off. To produce a second half-cycle of a CW-mode drive signal on the output 206, CW drive transistor Q5 216 and CW CNTRL transistor Q6 218 are turned on while transistors Q3 212 and Q4 214 are turned off. Thus, CW drive transistors Q4 214 and Q5 216 and corresponding CW CNTRL transistors Q3 212 and Q6 218 are alternately turned on and off for a predetermined time period as required to generate a square wave of the desired frequency on the output 206. Embodiments may generate the square wave continuously while CW-mode is enabled. Thus, CW drive transistors Q4 214 and Q5 216 are preferably employed both to generate a CW-mode ultrasonic drive signal on the output 206 and to shunt the output 206 to ground when no drive signal is being generated, for example, between B-mode pulses. Accordingly, embodiments of transmitter 104 preferably reduce the circuit area and the power dissipation of the transmitter by including an embodiment of the above described transmitter driver circuit 200 to provide both B-Mode and CW-mode drive signals.

An alternative embodiment of a transmitter drive circuit that uses the B-Mode drive transistors Q1 202 and Q2 204 with a variable +/−HV power supply to produce the CW-mode output results in increased power consumption due to the large currents required from drivers 208, 210 to continuously drive the transistors Q1 202 and Q2 204. Moreover, depending on the change rate of the +/−HV supply voltage from high to low voltage or vice verse the circuit can be subject to damaging electrical stress. Embodiments of the present disclosure, such as transmitter driver 200, advantageously avoid these shortcomings.

FIG. 3 shows an illustrative diagram of various signals produced when generating B-mode and CW-mode ultrasonic drive signals in accordance with various embodiments. The illustrative diagram begins, in period 302, with the transmitter driver 200 in shunt mode where the output 206 is clamped to ground through diodes D1 230, D2 226, D3 224, and D4 228 and transistors Q4 214 and Q5 216. Thus, signals T3 and T4 are asserted to enable transistors Q4 214 and Q5 216, and signals T1, T2, and CW CNTRL1 and CW CNTRL2 are negated to disable the associated drive transistors, Q1 202, Q2 204, and CW CNTRL transistors Q3 212 and Q6 218.

A B-mode pulse is generated in time period 304. To produce a B-mode pulse on output 206, the shunt transistors (i.e. CW drive transistors) Q4 214 and Q5 216 are turned off by negating T3 and T4 as illustrated. The CW control transistors Q3 212 and Q6 218 are disabled via CW CNTRL1 and CW CNTRL2 respectively. T1 is asserted to turn on drive transistor Q1 202 and generate a first polarity of B-mode pulse, while T2 is negated to turn off drive transistor Q2 204. Thereafter, T2 is asserted to turn on drive transistor Q2 204 and generate a second polarity of B-mode pulse, while T1 is negated to turn off drive transistor Q1 202. When the B-mode pulse is complete both of transistors Q1 202 and Q2 204 are turned off and, the shunt mode is re-engaged, in time period 306, as described above to bring the output 206 to ground. As a matter of simplification, a single B-mode pulse is illustrated, but embodiments may generate any number of pulses in period 304. In some embodiments, the timing of activation and deactivation of transistors Q1 202 and Q3 204 may be the reverse of that described above. Moreover, some embodiments may assert T3 and/or T4 between assertions of T1 and T2 to bring the output 206 to ground.

A CW-mode drive signal is illustrated in time period 308. To produce the CW-mode signal on output 206, the B-Mode drive transistors Q1 202 and Q2 204 are turned off by negating T1 and T2 as illustrated. In FIG. 3, T1 and T2 are already negated at the start of period 308, so they remain negated to maintain deactivation of Q1 202 and Q2 204. A first half-cycle of a CW-mode drive signal is produced by asserting CW CNTRL1 and T3 to activate CW CNTRL transistor Q3 212 and CW drive transistor Q4 214 respectively. Moreover, CW CNTRL2 and T4 are negated to deactivate CW CNTRL transistor Q6 218 and CW drive transistor Q5 216.

A second half-cycle of a CW-mode drive signal is produced by asserting CW CNTRL2 and T4 to activate CW CNTRL transistor Q6 218 and CW drive transistor Q5 216 respectively. CW CNTRL1 and T3 are negated to deactivate CW CNTRL transistor Q3 212 and CW drive transistor Q4 214 during the second half-cycle. First and second half-cycles are alternately generated in repetitive fashion to produce as many cycles of the CW drive signal on output 206 as are desired.

FIG. 4 shows a flow diagram for a method for generating a B-mode ultrasonic drive signal and a CW-mode ultrasonic drive signal in accordance with various embodiments. Though depicted sequentially as a matter of convenience, at least some of the actions shown can be performed in a different order and/or performed in parallel. Additionally, some embodiments may perform only some of the actions shown. In block 402, the transmitter 200 is producing no ultrasonic drive signal, and consequently the shunt mode is enabled. The shunt transistors (i.e., the CW drive transistors), Q4 214 and Q5 216 are turned on, the B-mode drive transistors Q1 202 and Q2 204 are turned off, and the CW-mode control transistors Q3 212 and Q6 218 are turned off.

If a CW-mode ultrasonic drive signal is to be produced, as determined in block 404, then, in block 408, the CW drive circuits are configured to drive a negative half-cycle of the CW drive waveform onto output 206. The first CW CNTRL transistor Q3 212 is turned on allowing current to flow to the CW drive transistor Q4 214. The CW drive transistor Q4 214 is turned on to drive −CW voltage onto output 206, and the second CW CNTRL transistor Q6 218 and the second CW drive transistor Q5 216 are turned off.

In block 412, the CW drive circuits are configured to drive a positive half-cycle of the CW drive waveform onto output 206. The second CW CNTRL transistor Q6 218 is turned on allowing current to flow to the CW drive transistor Q5 216. The CW drive transistor Q5 216 is turned on to drive +CW voltage onto output 206, and the first CW CNTRL transistor Q3 212 and the second CW drive transistor Q4 214 are turned off.

Blocks 408 and 412 are repeated to generate a continuous CW drive signal until CW-mode signal generation is disabled in block 414. Thus, the frequency of the CW-mode drive signal is determined by the rate at which the CW drive transistors Q4 214 and Q5 216, and corresponding CW CNTRL transistors Q3 212 and Q6 218 are enabled and disabled. When CW-mode signal generation is discontinued, in block 414, the transmitter 200 enters the shunt mode in block 402.

If a B-mode ultrasonic drive signal is to be produced, as determined in block 406, then the shunt transistors (i.e., the CW drive transistors) Q4 214 and Q5 216 are turned off in block 416. In block 418, a first polarity of a B-mode drive pulse is generated by turning on B-mode drive transistor Q1 202 and turning off B-mode drive transistor Q2 204. A second polarity of a B-mode drive pulse is generated, in block 420, by turning on B-mode drive transistor Q2 204 and turning off B-mode drive transistor Q1 202. Some embodiments generate a desired number of B-mode pulses by repeating blocks 418-420. When the B-mode pulse is complete, B-mode drive transistors Q1 202, Q2 204 are turned off, and the shunt transistors (i.e., the CW drive transistors) Q4 214 and Q5 216 are turned on, in block 422, to pull the output 206 to ground. In some embodiments, the shunt transistors, Q4 214 and Q5 216, are enabled for a time interval between generation of the first and second polarities (i.e., blocks 422 and 416 are inserted between blocks 418 and 420). Some embodiments generate a desired number of B-mode pulses of one polarity by iterating blocks 416-422 and performing the operations of only one of blocks 418 and 420. If B-mode drive is to be discontinued, in block 424, then the transmitter 200 enters the shunt mode in block 402. Otherwise, after a predetermined time delay expires, in block 426, B-mode drive signal generation continues in block 416.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An ultrasound transmitter, comprising:
a first shunt transistor, coupled to a first signal, that shunts positive transmitter output voltage to ground;
a first continuous wave CW control transistor coupled to the first shunt transistor and a first continuous wave control signal;
a second shunt transistor, coupled to a second signal, that shunts negative transmitter output voltage to ground;
a second continuous wave CW control transistor coupled to the second shunt transistor and a second continuous wave control signal; and
the shunt transistors comprise control inputs that, when modulated, cause the shunt transistors to produce a continuous wave ultrasonic drive signal on a transmitter output;
wherein the first and second CW control transistors respectively provide negative and positive CW drive voltage to the first and second shunt transistors.

2. The ultrasound transmitter of claim 1, further comprising:
a pair of B-mode drive transistors Q1 (202) and Q2 (204) coupled to the first and second shunt transistors that generates a B-mode ultrasonic drive pulse;
wherein both B-mode driver transistors Q1 (202) and Q2 (204) are disabled to allow generation of a CW-mode ultrasonic drive signal.

3. The ultrasound transmitter of claim 1, further comprising:
a first rectifying device coupled from the first shunt transistor and the first CW control transistor to ground; and
a second rectifying device coupled from the second shunt transistor and the second CW control transistor to ground.

4. The ultrasound transmitter of claim 1, wherein the CW control transistors and the shunt transistors are disabled by a pair of B-mode driver transistors Q1 (202) and Q2 (204) to allow generation of a B-mode ultrasonic drive signal.

5. The ultrasound transmitter of claim 1, further comprising:
negative and positive high-voltage ("HV") power supplies respectively coupled to first and second B-mode driver transistors Q1 (202) and Q2 (204); and
negative and positive CW power supplies respectively coupled to the first and second CW control transistors;
wherein the CW power supply output voltages are lower that the HV power supply output voltages.

6. The ultrasound transmitter of claim 1, wherein the first shunt transistor and the second shunt transistor are alternately enabled to generate the CW ultrasonic drive signal.

7. A method, comprising:
enabling a first continuous wave ("CW") control transistor coupled to a CW voltage allowing a current to flow to a first CW drive transistor coupled to the CW control transistor;
enabling the first CW drive transistor to drive the CW voltage onto an output;
disabling a second CW drive transistor coupled to the output and a second CW control transistor; and
providing a CW ultrasonic drive signal to an acoustic transducer via the output.

8. The method of claim 7, further comprising:
disabling the first CW drive transistor; and
enabling the second CW drive transistor.

9. The method of claim 7, further comprising enabling a CW output drive signal, at least in part, by disabling a pair of B-mode drive transistors Q1 (202) and Q2 (204).

10. The method of claim 7, further comprising enabling a B-mode output drive signal, at least in part, by disabling the first and second CW drive transistors and the CW control transistor.

11. The method of claim 7, further comprising:
disabling ultrasonic output by:
enabling the first and second CW drive transistors;
disabling the CW control transistors; and
disabling a pair of B-mode drive transistors Q1 (202) and Q2 (204) coupled to the output.

12. The method of claim 11, further comprising shunting voltage on an ultrasonic transmitter output to ground through the CW drive transistors.

13. An ultrasound imaging system, comprising:
an ultrasonic signal receiver coupled to a transducer system and a signal processor, the transducer system for converting a plurality of detected waves into electrical signals;
an ultrasonic signal transmitter coupled to the transducer system, said transmitter comprising:
means for generating a continuous wave ("CW") ultrasonic drive signal through a transmitter shunt transistor;
means coupled to a CW power supply voltage and to the shunt transistor for providing the CW power supply voltage to the transmitter shunt transistor; and
means for protecting a CW control transistor coupled to the shunt transistor from an ultrasonic drive voltage generated by a B-mode drive circuit coupled to the shunt transistor.

14. The ultrasound imaging system of claim 13, wherein all B-mode drive circuits are disabled during generation of the CW ultrasonic drive signal.

15. The ultrasound imaging system of claim 13, wherein all CW-mode drive circuits are disabled during generation of a B-mode drive pulse.

16. The ultrasound imaging system of claim 13, wherein the means for generating an ultrasonic signal alternately enables each transistor of a pair of transmitter output shunt transistors.

17. The ultrasound imaging system of claim 13, wherein a means for providing a B-mode power supply voltage to a B-mode ultrasonic driver is separate from the means for providing a CW power supply voltage to the transmitter shunt transistor.

* * * * *